United States Patent [19]

Katayama et al.

[11] 4,123,426

[45] Oct. 31, 1978

[54] PROCESS FOR DECOMPOSING MICROBIAL CELLS

[75] Inventors: Masao Katayama, Niigata; Yataro Tabeta, Tokyo, both of Japan

[73] Assignees: Mitsubishi Gas Chemical Company, Inc.; Daiichi Kasei Sangyo Co., Ltd., both of Japan

[21] Appl. No.: 821,316

[22] Filed: Aug. 2, 1977

[30] Foreign Application Priority Data

Aug. 5, 1976 [JP] Japan .................................. 51-93833

[51] Int. Cl.$^2$ ........................... A23J 1/18; C07G 7/00
[52] U.S. Cl. ................................. 260/112 R; 252/350
[58] Field of Search .................................... 260/112 R

[56] References Cited

U.S. PATENT DOCUMENTS

| 3,585,179 | 6/1971 | Samejima et al. ............... 260/112 R |
| 3,718,541 | 2/1973 | Kalina ................................ 195/28 R |
| 3,862,109 | 1/1975 | Mitsuda et al. .................... 260/112 R |
| 3,878,093 | 4/1975 | Kanani et al. ................. 260/112 R X |
| 3,962,466 | 6/1976 | Nakabayashi ............... 260/112 R X |
| 3,983,008 | 9/1976 | Shinozaki et al. ........... 260/112 R X |

FOREIGN PATENT DOCUMENTS

| 8,336,873 | 3/1975 | Japan. |
| 2,105,755 | 7/1957 | Japan. |
| 3,263,255 | 9/1957 | Japan. |

OTHER PUBLICATIONS

Chem. Absracts vol. 84, 1976, 92358H, Katsayama.

*Primary Examiner*—Howard E. Schain
*Attorney, Agent, or Firm*—Wenderoth, Lind & Ponack

[57] ABSTRACT

Foamable hydrolyzed proteins substantially free from lipid, nucleic acids, and nucleic acid related substances are obtained by decomposing microbial cells with an alkaline aqueous solution containing an alkaline earth metal hydroxide and an alkali metal hydroxide. The hydrolyzed proteins are useful as foaming agents, especially fire-extinguishing foams effective against fires of oils. The starting microbial cells are available at low cost in great quantities.

4 Claims, 2 Drawing Figures

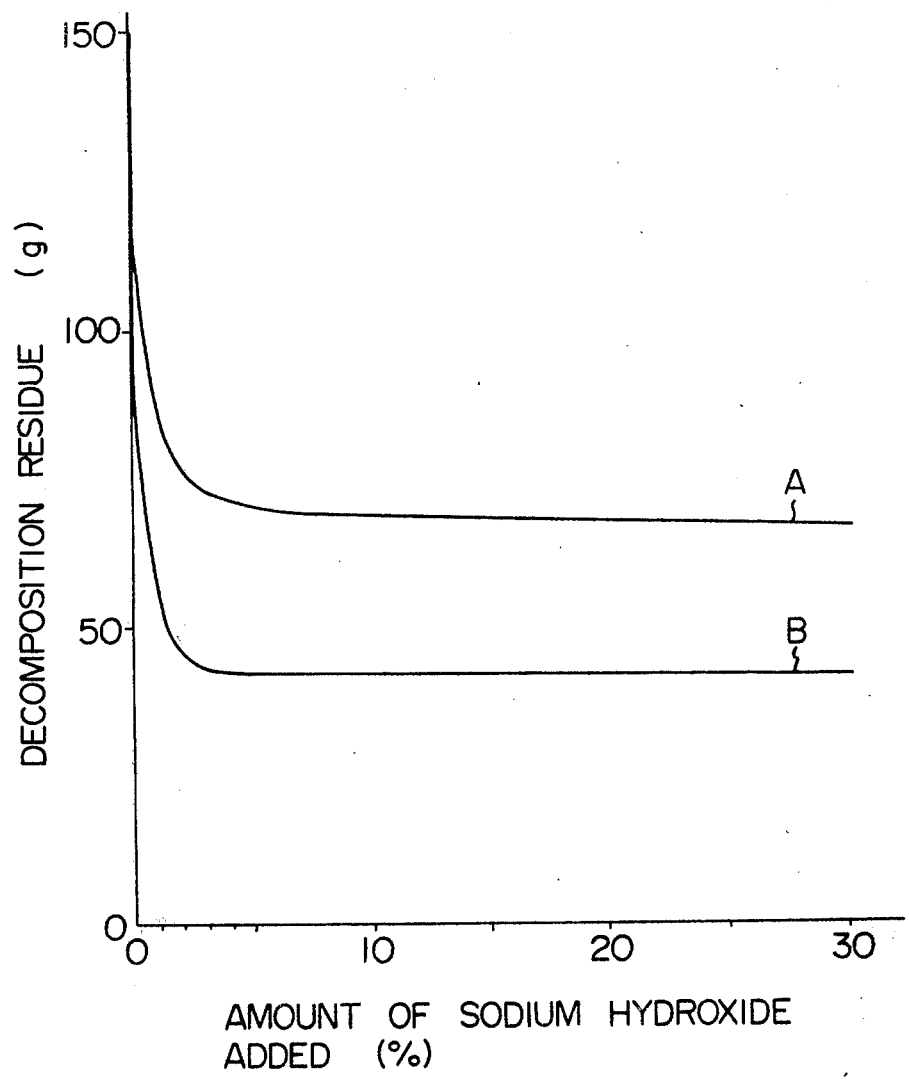

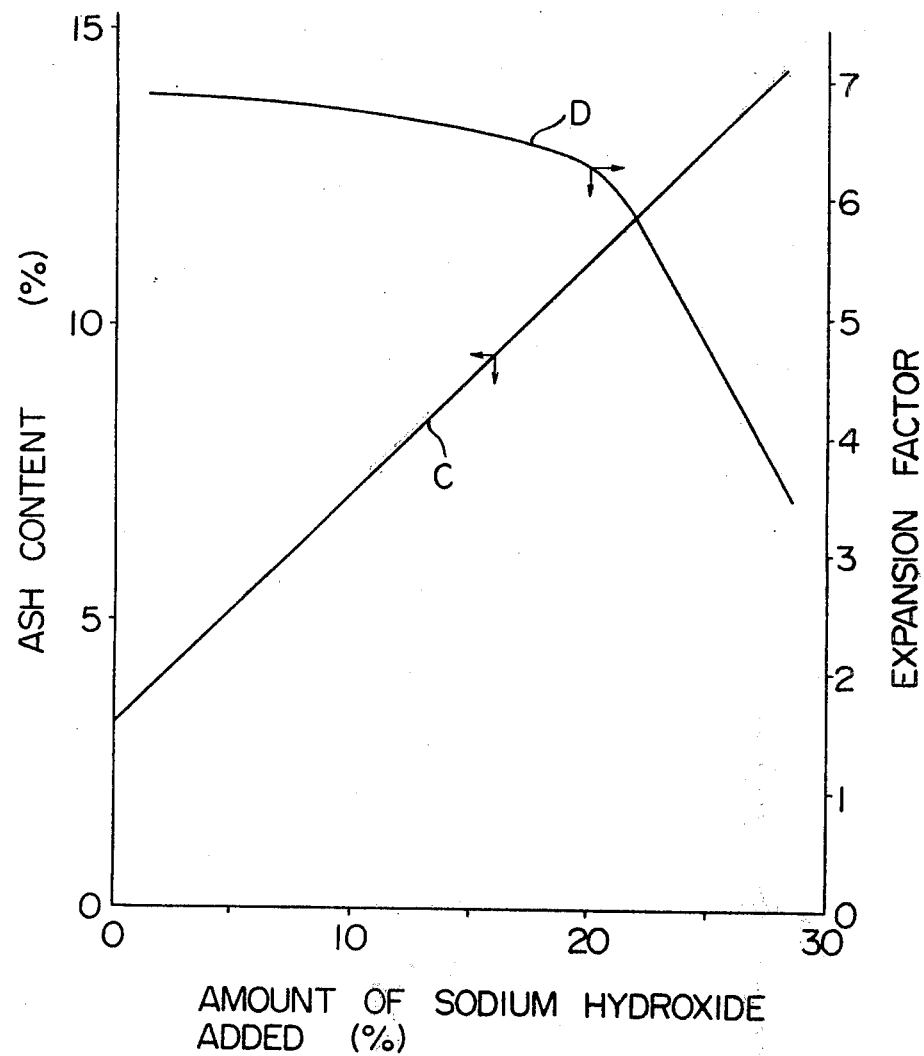

PROCESS FOR DECOMPOSING MICROBIAL CELLS

FIELD OF THE INVENTION

This invention relates to a process for decomposing microbial cells, and more specifically, to a process for producing partial hydrolyzates of proteins which are substantially free from lipid, and nucleic acids and their related substances and are suitable for use as a foaming agent, especially as foam fire-extinguishers based on hydrolyzed proteins.

BACKGROUND OF THE INVENTION

Regulations of the Ministry of Home Affairs, Japan describe hydrolyzed protein-based foams, synthetic detergent foams and aqueous film-forming foams as three types of fire-extinguishing foams. The protein-based foams exhibit by far the best effect against fires of petroleums, especially conflagration of oil tanks.

Conventional protein-based fire-extinguishing foams produced in Japan start from meals (keratin) of hoofs and horns of horses and bovines as raw materials. For example, Japanese Patent Publication No. 7896/57 discloses a method for producing such a fire extinguisher, which comprises adding sodium hydroxide and water to a hoof and horn meal, heating the mixture at about 100° C. for several hours to hydrolyze proteins partially, adding an inorganic acid such as hydrochloric acid or sulfuric acid or an organic acid such as oxalic acid or acetic acid to neutralize it, removing insoluble substances, concentrating the residue to a suitable concentration, and incorporating additives for imparting oil resistance, heat resistance and foam stability, for example by adding several percent of a ferrous salt such as ferrous sulfate or ferrous chloride, an antiseptic such as benzoic acid or pentachlorophenol sodium salt, and an anti-freezing agent such as ethylene glycol or propylene glycol.

Since the hoof and horn meal used as a raw material in the above method is a scleroprotein, its hydrolysis requires a period of several hours, and at times, it is necessary, as disclosed in Japanese Patent Publication No. 3643/64, to heat-treat it at 80° to 130° C. for 1 to 8 hours prior to hydrolysis. Furthermore, since hoof and horn meals contain large quantities of sulfur-containing amino acids, they give off marked offensive odors during alkali decomposition, and the final decomposition products also smell extremely bad. Since the hoof and horn meals are naturally occurring substances most of which are imported from South East Asia and China, the supply of these goods is unstable both in cost and in quantity, and their quality also varies greatly.

In recent years, single-cell organisms or microbial cells which can be produced commercially in large quantities have attracted attention as protein sources that will replace the hoof and horn meals. Methods have already been proposed to produce fire-extinguishing foams and other types of foams by hydrolyzing microbial cells with an alkali such as calcium hydroxide or sodium hydroxide. This alkali hydrolysis is usually performed by adding 15 to 50% by weight of calcium hydroxide or sodium hydroxide to the microbial cells, adding water to a cell concentration of 10 to 30%, and heating the mixture at 100° C. for at least several hours.

When microbial cells are decomposed with alkalies, however, their organic ingredients such as lipid, carbohydrates, and nucleic acids and their related substances, and their inorganic ingredients such as phosphorus, potassium and calcium, which are present in amounts of several percent to several tens of percent, present various difficulties.

When only sodium hydroxide is used as an agent for hydrolysis, a ferrous salt which is added to the filtrate left after the removal of the alkali decomposition residue is almost entirely precipitated and wasted, and the hydrolyzate gels on cooling. To avoid these difficulties, Japanese Laid-Open Patent Publication No. 31698/75 suggests the hydrolysis of microbial cells after heat-treating them in an acid aqueous solution. This method can prevent the formation of a precipitate at the time of neutralization and of adding a ferrous salt, but since the hydrolyzate still gels, it should be further treated to remove lipid.

Accordingly, in order to hydrolyze microbial cells using sodium hydroxide alone, a chemical treatment such as heat-treatment in acidity and a lipid-removing treatment are required, and this method cannot be applied to untreated microbial cells or to cells subjected to enzymatic treatment or a physical treatment. Furthermore, in the hydrolysis of microbial cells heat-treated in an acid aqueous solution using sodium hydroxide, the sodium hydroxide used is converted to a salt of an organic acid such as sodium oxalate or a salt of an inorganic acid such as sodium chloride or sodium sulfate by the subsequent neutralization treatment, and remains in the resulting fire-extinguishing foams. As a result, the concentration of salts in the fire-extinguishing foams increases, and the concentration of the protein hydrolyzate as a main ingredient decreases relatively. This adversely affects the performance of the fire-extinguishing foams, especially their foaming properties.

On the other hand, the present inventors have found that when only calcium hydroxide is used, untreated microbial cells are scarcely hydrolyzable even if heat-treated for long periods of time. It is difficult to hydrolyze the cells even if 30% by weight of calcium hydroxide and 500% by weight of water are added to the microbial cells, and the mixture is heat-treated at 100° C. for 10 hours. When as disclosed in Japanese Laid-Open Patent Publication No. 31698/75, the microbial cells are hydrolyzed after they have been heat-treated in an acid aqueous solution (pH not more than 1.5), the apparent volume of the solution during decomposition expands by foaming to 2 to 3 times to make its stirring difficult. Moreover, the amount of the alkali hydrolysis residue is large, and the yield of the protein hydrolyzate in the filtrate after removal of the residue is reduced.

It is an objective of this invention to provide a process for hydrolyzing microbial cells which removes the defects of the aforesaid conventional techniques, hydrolyzes proteins in the microbial cells rapidly and uniformly at high conversions, remove other ingredients of the cells, such as lipid, phosphoric acid, and nucleic acids and their related substances, is simple in post-treatment after hydrolysis, and can be suitably used to produce hydrolyzed protein-based fire-extinguishing foams, concrete foaming agents, and other types of foaming agents.

The present invention is based on the discovery that when microbial cells are subjected to a hydrolyzing treatment by using a combination of an alkaline earth metal hydroxide and an alkali metal hydroxide, most of the lipid, phosphoric acid, nucleic acids and their related substances move to the alkali hydrolysis residue, and scarcely remain in the filtrate after removal of the residue.

SUMMARY OF THE INVENTION

The present invention provides a process for decomposing microbial cells to obtain foamable hydrolyzed proteins, which comprises treating the microbial cells with an aqueous solution containing an alkaline earth metal hydroxide and an alkali metal hydroxide.

In a preferred embodiment of this invention, the hydrolysis residue is removed subsequent to the decomposition of the microbial cells; the pH of the resulting filtrate is adjusted to 3–7.5 to coagulate and separate the unreacted proteins, etc.; and a carbonic acid compound is added under alkalinity to the supernatant liquid to separate and remove the dissolved alkaline earth metal compound as an alkaline earth metal carbonate.

BRIEF DESCRIPTION OF THE DRAWINGS

FIG. 1 is a diagram showing the relation between the amount of sodium hydroxide used in decomposing microbial cells and the weight of the hydrolysis residue; and FIG. 2 is a diagram showing the relation of the amount of sodium hydroxide used in hydrolyzing microbial cells to the ash content of the concentrate obtained after post-treating the hydrolyzate and to the expansion factor of the concentrate.

DETAILED DESCRIPTION OF THE INVENTION

The microbial cells used in this invention may be cells of a single species or a mixture of two or more species of any microorganisms, for example, yeasts of the genus Saccharomyces, Candida, Torula and Pichia, bacteria of the genus Pseudomonas, Bacillus, Protaminobacter, Corynebacterium and Brevibacterium, Actinomycetes, and molds. They may be living cells separated from the culture broth, or dry cells obtained by drying the living cells. Generally, the bacteria are advantageous because of their higher crude protein content. The microbial cells used in this invention also include microbial cell-containing materials such as excess sludge from the treatment of activated sludge, and fermentation residues from the fermentation industry such as the fermentation of amino acids. There can also be used treated products of these microbial cells, for example those submitted to a chemical treatment (for example, treatment with acids, alkalies, salt water, etc.), an enzymatic treatment (for example, enzymatic attack of the cell walls), a physical treatment (for example, ultrasonic disintegration, treatment with a French press, disruption in a vibratory glass bead mill, etc.), and/or a heat-treatment (for example, dry heat treatment, steaming treatment, hot water treatment, etc.). Separated proteins obtained by treating microbial cells with acids or alkalies to extract proteins, and then precipitating them at their isoelectric point can also be used in this invention.

A method for obtaining a foamable hydrolyzed protein by hydrolyzing the microbial cells with an alkali aqueous alkali solution is known. The characteristic feature of the present invention is to use specified amounts of an alkali metal hydroxide and an alkaline earth metal hydroxide as the alkali in such a method.

Examples of the alkali metal hydroxide are lithium hydroxide, sodium hydroxide and potassium hydroxide, and examples of the alkaline earth metal hydroxide are calcium hydroxide, magnesium hydroxide, barium hydroxide and strontium hydroxide. They can be used either singly or as mixtures of two or more. Especially preferred alkalies are sodium hydroxide, potassium hydroxide, calcium hydroxide, magnesium hydroxide and barium hydroxide. Compounds which will form alkaline earth hydroxides in an alkaline aqueous solution, such as their chlorides (e.g., magnsium chloride) and their oxides (e.g., magnesium oxide) can also be used.

The alkali metal hydroxide and the alkaline earth metal hydroxide may be added simultaneously or separately. For example, the microbial cells are hydrolyzed to some degree in an aqueous solution of the alkali metal hydroxide, and then the alkaline earth metal hydroxide is added, after which the reaction is further performed in the mixed solution. For commercial operation, the simultaneous addition of these alkaline solutions is preferred.

The amounts of the alkaline earth metal hydroxide and the alkali metal hydroxide are generally 15 to 50% by weight and 2 to 20% by weight, respectively, based on the weight of the dry microbial cells or separated proteins (unless otherwise specified, the amounts are based on the weight of the dry microbial cells or separated proteins throughout the specification). Suitable amounts are chosen within these ranges according to the type of the microbial cells, whether to perform the pre-treatment of the cells, the type of the pre-treatment, etc. For example, when untreated microbial cells are used as raw materials, the suitable amounts of the alkaline earth metal hydroxide and the alkali metal hydroxide are 15 to 40% by weight, and 5 to 20% by weight, respectively. When microbial cells subjected to a chemical treatment such as heat-treatment in acidity or separated proteins are used as raw materials, the preferred amounts of the alkaline earth metal hydroxide and the alkali metal hydroxide are 15 to 50% by weight, and 2 to 15% by weight, respectively.

When the amount of the alkaline earth metal hydroxide does not reach 15% by weight, ingredients other than proteins, such as lipid, phosphoric acid, and nucleic acids and their related substances, cannot be fully precipitated. When the amount of the alkali metal hydroxide does not reach 2% by weight, it is impossible to fully hydrolyze even chemically pre-treated (heat-treated in acidity) microbial cells which are relatively easy to hydrolyze, and the residue left after hydrolysis (to be referred to as the hydrolysis residue) increases abruptly to cause commercial disadvantage.

One example of experimental results in this regard is described with reference to FIG. 1 which shows the amount of the hydrolysis residue (the weight obtained by drying at 100° C. to a constant weight) per 100 g of the starting microbial cells at the time of hydrolyzing the microbial cells with an aqueous solution containing 35% by weight of calcium hydroxide and 0 to 30% by weight of sodium hydroxide, both based on the weight of the microbial cells. Curve A refers to the case of using untreated microbial cells, and the curve B, to the case of using acid heat-treated microbial cells. The hydrolysis in this case was performed for 8 hours with a cell concentration of 17% by weight.

It is seen from FIG. 1 that both in curves A and B, the amount of the hydrolysis residue increases abruptly when the amount of sodium hydroxide is less than about 2% by weight. The hydrolysis residue contains unreacted calcium hydroxide, undecomposed microbial cells, calcium phosphate, calcium salts of fatty acids, etc.

On the other hand, when the amount of the alkaline earth metal hydroxide exceeds 50% by weight, the amount of the unreacted hydroxide increases after the hydrolysis, and an extra step of removing it by filtration is required. Moreover, there is no substantial need to use it in an amount larger than 50% by weight.

When the amount of the alkali metal hydroxide exceeds 20% by weight, the hydrolysis of proteins generally proceeds excessively although it depends upon the amount of water added (in other words, the concentration of alkali), and a non-uniform protein hydrolyzate results. This adversely affects the performance of hydrolyzed protein-based fire-extinguishing foams. Furthermore, the alkali metal hydroxide used is changed to a chloride, sulfate, or oxalate by a neutralizing treatment in a subsequent step, and remains in the hydrolyzate. This also causes the deterioration of the properties of hydrolyzed protein-based fire-extinguishing foams.

An experimental result in this regard is shown in FIG. 2. Microbial cells heat-treated in acidity are hydrolyzed at 100° C. for 8 hours using an aqueous solution containing 35% by weight of calcium hydroxide and 0 to 25% by weight of sodium hydroxide. The filtrate after the removal of the residue is neutralized to a pH of 6.8, and concentrated until its specific gravity becomes 1.18 (20° C.). The ash content of the concentrate (straight line C) and the expansion factor of a fire extinguisher foam containing 3% of hydrolyzed proteins at the time of adding 0.4% by weight, as $Fe^{2+}$, of ferrous chloride to the concentrate (curve D) are shown in FIG. 2. It can be seen from the straight line C that with increasing amount of sodium hydroxide, the ash content of the concentrate increases. Furthermore, it can be seen from curve D that when the amount of sodium hydroxide exceeds 20% by weight, the expansion factor abruptly decreases.

The ratio between the alkaline earth metal hydroxide and the alkali metal hydroxide differs according, for example, to the type of the microbial cells, and the pretreating conditions. For example, when untreated microbial cells are used, it is advantageous to use the alkali metal hydroxide in a larger amount than in the case of using chemically pretreated microbial cells, because the untreated cells have rigid cellular walls and contain large amounts of nucleic acids and their related substances. In the case of chemically pretreated microbial cells or separated proteins, it is advantageous to use the alkali metal hydroxide in a smaller amount because they contain lesser amounts of the aforesaid substances. Preferably, therefore, the ratio between the alkaline earth metal hydroxide and the alkali metal hydroxide is generally higher for pre-treated microbial cells and separated proteins than for untreated microbial cells.

Usually, the amount of water used in the hydrolysis of microbial cells is suitably 200 to 1000% by weight based on the microbial cells. Hydrolysis proceeds by heating the resulting liquid generally at 90° to 120° C., preferably 95° to 100° C. The heating time, which is properly chosen according to the type of the microbial cells, the presence or absence of pretreatment, the pretreating conditions, the amount and concentration of the alkali metal hydroxide, and the desired properties of the fire-extinguishing foam, is generally about 4 to 10 hours.

Treatment of microbial cells under the conditions described hereinabove results in the partial hydrolysis of proteins in the cells to foaming components such as proteose and peptone. Ingredients other than proteins, such as lipid, can be removed finally as a hydrolysis residue. Nucleic acids and their related substances change to nucleosides and nucleic acid-forming bases. In the hydrolysis process in accordance with the process of this invention, the phosphoric acid linkages of deoxyribonucleic acid (DNA) customarily considered to be relatively stable to alkali are partly broken as are those of ribonucleic acid (RNA). These substances formed by hydrolysis are amphoteric compounds, and almost entirely remain in the filtrate at the time of removing the hydrolysis residue. Since, however, these substances have decreased solubility when the aqueous solution becomes neutral in the subsequent step, they finally precipitate by concentration. Moreover, some of the nucleosides form insoluble compounds with alkaline earth metals, and finally move to the hydrolysis residue. Furthermore, since the filtrate left after the removal of the hydrolysis residue scarcely contains lipid, phosphates and nucleic acid-related substances, the hydrolyzate does not gel on cooling. Even when a metal salt such as a ferrous salt is added to the concentrated hydrolyzate, no precipitate is formed.

In a conventional method in which hydrolysis is performed using an alkali metal hydroxide alone, the alkali metal reacts with phosphoric acid formed as a result of hydrolysis and becomes an alkali metal phosphate which remains in the filtrate left after the removal of the hydrolysis residue. If a metal salt such as ferrous salt is added while the alkali metal phosphate is still present, almost all the added metal salt precipitates as a phosphate and the resulting product does not possess the properties of a foaming agent. However, in the present invention, the water-soluble alkali metal phosphate changes to a water-insoluble alkaline earth metal phosphate which can then be separated and removed. Addition of a metal salt such as a ferrous salt, therefore, does not form any precipitate.

After the hydrolysis of microbial cells, the resulting hydrolyzate is subjected to a solid-liquid separating means such as centrifugal separation or filtration on diatomaceous earth to remove the undecomposed matter, the unreacted alkaline earth metal hydroxide, and the reaction product.

In the present invention, an inorganic acid such as hydrochloric acid or sulfuric acid, or an organic acid such as oxalic acid or acetic acid is further added to the aforesaid filtrate to adjust its pH to 3 to 7.5 to precipitate the undecomposed proteins and nucleic acid related substances (the precipitate formed is referred to as an isoelectric point precipitate). When the pH is higher than 7.5, scarcely any precipitate is formed at the time of adjusting the pH. Preferably, the pH of the filtrate is not more than 5. When the pH is higher than 5, a precipitate of the undecomposed proteins forms, but only to an insufficient degree. Furthermore, nucleic acid related substances such as nucleosides, purine bases and pyrimidine bases do not sufficiently precipitate, and at times, form a precipitate during or after concentration. When the pH is lower than 3, the solubilities of the undecomposed proteins and of nucleic acid related substances increase, and they again dissolve. Hence, for practical purposes, it is preferred to adjust the pH of the filtrate to 3 to 5.

The filtrate (to be referred to as a neutralization filtrate) left after the removal of the isoelectric point precipitates contains only small amounts of impurities in addition to the partial hydrolyzates of proteins. A part of the partial hydrolyzate of proteins exists as an alkaline earth metal salt in the neutralization filtrate. It also includes a very small amount of an alkaline earth metal salt formed by neutralization. It is necessary to remove these alkaline earth metal salts because they precipitate during concentration or during the storage of a hydrolyzed protein-based fire-extinguishing foam as a final product.

In order to remove the alkaline earth metal salt from the neutralization filtrate, a carbonic acid compound is added after adjusting the pH of the filtrate to a value higher than 7, preferably 7.5 to 9. If the pH is adjusted to 7 or less, the carbonic acid compound is wasted. Preferred carbonic acid compounds are carbonates of ammonium such as ammonium carbonate, ammonium bicarbonate and ammonium carbamate. The amount of the carbonic acid compound is made larger than the stoichiometrical amount required to convert the alkaline earth metal salt dissolved in the neutralization filtrate to an insoluble alkaline earth metal carbonate. If the amount of the carbonic acid compound is less than the stoichiometrical amount, the alkaline earth metal salt still dissolves in the neutralization filtrate. The solubility of the resulting alkaline earth metal carbonate is extremely low. When carbonates of ammonium are used, the excess of the ammonium carbonates easily decomposes to carbon dioxide gas and ammonia by heating to a temperature of at least 50° C. Accordingly, there is substantially no carbonate of ammonia which moves to the final product. Similar results are obtained by blowing carbon dioxide into the neutralization filtrate while maintaining its pH at 8 to 9 or higher by adding ammonia.

After adding a carbonic acid compound to the neutralization filtrate, the mixture is preferably heated to complete the reaction of converting the alkaline earth metal to a carbonate, grow the crystals of the formed precipitate, and to decompose the excess of the carbonic acid compound. The heating temperature is usually 50° to 100° C., preferably 60° to 80° C. At these temperatures, the heating time is usually at least 30 minutes, preferably 1 to 2 hours.

The filtrate resulting after separating the alkaline earth metal carbonate by filtration is concentrated to the desired concentration, for example to a specific gravity of 1.1 to 1.2 (20° C.) by evaporation or otherwise. The resulting concentrate (to be referred to as "concentrated hydrolyzate") is generally used as a foaming agent. If a metal salt such as ferrous sulfate, an antiseptic such as pentachlorophenol sodium salt, and an antifreezing agent such as ethylene glycol are added to the concentrated hydrolyzate to form hydrolyzed protein-based fire-extinguishing foams or concrete foaming agents can be obtained. If amines, metal salts of fatty acids, saponin, etc. are added to the concentrated hydrolyzate, hydrolyzed protein-based fire-extinguishing foams having alcohol resistance can be obtained.

By hydrolysis with a combination of an alkaline earth metal hydroxide and an alkali metal hydroxide in accordance with the process of this invention, not only conventional chemically pretreated microbial cells, but also other microbial cells such as untreated microbial cells, physically pretreated microbial cells, enzymatically digested microbial cells, and microbial cell-containing materials, or separated proteins can be easily decomposed. At the same time, substances other than proteins, such as lipid, nucleic acids and nucleic acid-related substances, can be precipitated and removed, and subsequent treatments in the step of concentrating, desalinating, etc. can be simplified.

Products obtained in accordance with a preferred embodiment of this invention have uniform quality and are stable both in quantity and price, because the raw materials are microbial cells which can be produced commercially. They neither give off offensive odors unlike the case of using keratin as a raw material, and they have superior storage stability and foaming properties sufficiently conforming to the technical standards set forth in the Fire-Fighting Regulations.

The following Examples illustrate the present invention in more detail. The Japanese Underwriter's Standards referred to in the examples are the Standards of Fire and Marine Insurance Rating Association of Japan.

EXAMPLE 1

Water was added to dry cells of a methanol-assimilating bacterium (Pseudomonas japonica Su-18, FERM P-2182) to form a suspension having a concentration of 20% by weight, and 25% by weight of calcium hydroxide and 20% by weight of sodium hydroxide, both based on the caterial cells, were added. The mixture was heated at about 100° C. for 8 hours to decompose the cells. The liquid obtained was then cooled, and centrifuged to remove insoluble substances. Sulfuric acid was added to the filtrate to neutralize it to a pH of 7, and concentrated by evaporation. A small amount of a precipitate formed during the concentration. The precipitate was separated by filtration. The concentrating operation was continued, and stopped when the specific gravity of the concentrated solution reached 1.18 (20° C.). After cooling, a 30% by weight aqueous solution of ferrous sulfate was added to a concentration of 0.3% by weight as $Fe^{2+}$ to form a clear solution. The concentrated solution had a total phosphorus content of 0.3% by weight, and the starting bacterial cells had a total phosphorus content of 2.7% by weight. Accordingly, most of phosphorus moved to the decomposition residue. The lipid content of the concentrated hydrolyzate was 0.5% by weight, and the starting bacterial cells contained 8% by weight of lipid. Thus a greater part of the lipid moved to the hydrolysis residue.

Nucleic acids in the concentrated hydrolyzate were determined in accordance with the STS procedure (the Schmidt-Thannhauser-Schneider procedure). The total amount of ribonucleic acid (RNA) and deoxyribonucleic acid (DNA) was 0.9% by weight, and the starting bacterial cells contained 12.6% by weight of nucleic acids. Thus, most of nucleic acids moved to the hydrolysis residue.

EXAMPLE 2

Water was added to the same bacterial cells as used in Example 1 to form a 10% by weight suspension. Its pH was adjusted to 1.2 by adding sulfuric acid, and the suspension was heat-treated at 85° to 90° C. for 20 minutes. After cooling, a 10% by weight aqueous solution of sodium hydroxide was added to adjust the pH of the solution to 4, and then the suspension was centrifuged. The supernatant liquid separated by centrifuging was discarded, and the treated cells were washed once with water.

The treated cells were decomposed and concentrated in the same way as in Example 1. The concentrated hydrolyzate had a total phosphorus content of 0.11% by weight, and the starting treated cells had a total phosphorous content of 1.2% by weight. Accordingly, most of phosphorus moved to the hydrolysis residue. Further, the concentrated solution had a lipid content of 0.8% by weight, and the starting treated cells contained 10.5% by weight of lipid. Accordingly, most of the lipid was removed.

The nucleic acid content of the concentrated hydrolyzate, determined in the same manner as in Example 1, was 0.3% by weight, and the starting cells contained 5% by weight of nucleic acids. Thus, most of nucleic acids moved to the decomposition residue.

COMPARATIVE EXAMPLE 1

Water was added to the same bacterial cells as used in Example 1 to form a 20% by weight suspension, and 20% by weight, based on the cells, of sodium hydroxide was added. The mixture was decomposed by heating at about 100° C. for 8 hours. The hydrolyzate gelled after cooling. It was then heated to 30° to 40° C., and a small amount of water was added to dissolve it. Sulfuric acid was added to neutralize the liquid to a pH of 7, whereupon a small amount of a precipitate formed. The liquid was filtered, and the filtrate was concentrated by evaporation. Since a small amount of a precipitate formed during concentration, it was separated by filtration, and concentration was continued. In the last stage of concentration, lipid which precipitated on the surface of the liquid was removed. Concentration was stopped when the specific gravity of the decomposition concentrate reached 1.12 (20° C.). The concentrate was cooled, and a 30% by weight aqueous solution of ferrous sulfate was added in an amount of 0.3% by weight as $Fe^{2+}$. A large quantity of a precipitate formed.

The results show that when sodium hydroxide is used alone, a precipitate is formed by addition of ferrous sulfate, and the product is unsuitable as a material for a foaming agent.

COMPARATIVE EXAMPLE 2

Water was added to the same pre-treated bacterial cells as used in Example 2 to form a 15% by weight suspension. Calcium hydroxide was added in an amount of 30% by weight based on the bacterial cells. The mixture was heated at about 100° C. for 10 hours to decompose the bacterial cells. At the time of decomposition, the suspension expanded to 2 to 4 times in volume by foaming, and became difficult to stir. After the decomposition, the product was cooled, and centrifuged to remove insoluble substances. The insoluble substances were dried at 100° C. to a constant weight. The dried weight was about 2 times as large as that in Example 2. Sulfuric acid was added to the supernatant liquid of the centrifugal separation to neutralize it to a pH of 7, thereby precipitating the calcium salt as calcium sulfate. The calcium sulfate was separated by filtration, and the filtrate was concentrated by evaporation until its specific gravity became 1.18 (20° C.). The yield of the concentrated hydrolyzate at this time was about 60% of that in Example 2.

EXAMPLE 3

Water was added to the same dried cells as used in Example 1 to form a 17% by weight suspension. To the suspension were added 18% by weight of barium hydroxide and 18% by weight of sodium hydroxide, both being based on the weight of the dry cells. The mixture was heated at about 100° C. for 8 hours to decompose the cells. The hydrolyzate was centrifuged after cooling to separate insoluble substances. Sulfuric acid was added to the supernatant liquid of the centrifugal separation to adjust its pH to 6.5. The resulting precipitate of barium sulfate, etc. was separated by filtration, and the filtrate was concentrated by evaporation. Since a small amount of a precipitate formed during the concentration, it was separated by filtration, and the concentration was continued. When the specific gravity of the concentrate reached 1.14 (20° C.), the concentration was stopped. After cooling, pentachlorophenol sodium salt, ferrous sulfate and ethylene glycol were added, and the pH of the mixture was adjusted to 7 to form a 6% hydrolyzed protein-based fire-extinguishing foam.

According to the tests specified by the Japanese Underwriter's Standards, this fire-extinguishing foam exhibited an expansion factor of 6.2 and a fire resistance of 5 minutes 40 seconds, and well met the above Standards.

EXAMPLE 4

Water was added to the same dry cells as used in Example 1 to form a 15% by weight suspension. To the suspension were added 20% by weight of calcium hydroxide, 5% by weight of magnesium chloride and 15% by weight of potassium hydroxide, all being based on the weight of the dry cells. The mixture was heated at about 100° C. for 7 hours to decompose the cells. The hydrolyzate was hot-filtered through diatomaceous earth to separate insoluble substances. Hydrochloric acid was added to the filtrate to neutralize it to a pH of 6.0. The resulting precipitate was separated by filtration, and the filtrate was concentrated by evaporation. A small amount of a precipitate which formed during the concentration was separated by filtration, and the concentrating operation was continued. When the specific gravity of the concentric reached 1.18 (20° C.), the concentrating operation was stopped. The concentrate was cooled, and sodium benzoate, ferrous chloride and propylene glycol were added. The pH of the mixture was adjusted to 7 to form a 3% hydrolyzed protein-based fire-extinguishing foam. According to the tests by the Japanese Underwriter's Standards, this foam exhibited an expansion factor of 6.3, and a fire resistance of 5 minutes 20 seconds.

EXAMPLE 5

Water was added to dry cells of a methanol-assimilating bacterium (Pseudomonas japonica BC-145, FERM P-2183) to form a 10% by weight suspension. Hydrochloric acid was added to adjust its pH to 4, and the mixture was heat-treated at 80° to 85° C. for 2 hours. After cooling, the product was centrifuged, and washed once with water. Water was added to the pre-treated cells to form a 17% by weight suspension. Then, 15% by weight of sodium hydroxide and 30% by weight of calcium hydroxide, all based on the weight of the dry cells, were added to the suspension, and the mixture was heated at about 100° C. for 8 hours to decompose the cells. The hydrolyzate was hot-filtered through diatomaceous earth, and hydrochloric acid was added to the filtrate to adjust its pH to 5.5. A small amount of a precipitate which formed was separated by filtration, and the filtrate was concentrated. The precipitate which formed during the concentration was removed by filtration, and the concentration was continued. When the specific gravity of the concentrate reached 1.19 (20° C.), the concentration was stopped. The concentrate was cooled, and pentachlorophenol sodium salt, ferrous chloride and ethylene glycol were added.

The pH of the mixture was adjusted to 7 to afford a 3% hydrolyzed protein-based fire-extinguishing foam. According to the tests by the Japanese Underwriter's Standards, the foams exhibited an expansion factor of 6.5, and a fire resistance of 5 minutes 30 seconds, and fully met the above Standards.

COMPARATIVE EXAMPLE 3

A 3% hydrolyzed protein-based fire-extinguishing foam was prepared in the same way as in Example 5 except that the amounts of calcium hydroxide and sodium hydroxide used for hydrolysis were changed to 30% by weight, and 25% by weight respectively based on the weight of the dry bacterial cells. By the tests of the Japanese Underwriter's Standards, this foam exhibited an expansion factor of 4.2 which did not met the above Standards. Its fire resistance was 5 minutes 10 seconds, and met the above Standards.

EXAMPLE 6

Microbial cells were obtained by centrifugal separation from a culture broth of a methanol-assimilating yeast (Candida alcomigas IT-10, FERM P-1972). Water was added to the cells to form an 8% by weight suspension, and the cells were destroyed by a vibratory glass bead mill. To the disrupted cells were added 35% by weight of calcium hydroxide and 10% by weight of sodium hydroxide, all being based on the weight of the cells, and the mixture was heated at about 100° C. for 10 hours to decompose the cells. The product was hot-filtered through diatomaceous earth to separate water-insoluble substances. Hydrochloric acid was added to the resulting filtrate to neutralize it to a pH of 6, and then it was concentrated. The precipitate which formed during the concentration was separated by filtration, and the concentration was continued. When the specific gravity of the concentrate reached 1.15 (20° C.), the concentration was stopped. The concentrate was cooled, and pentachlorophenol sodium salt, ferrous chloride and ethylene glycol was added. The pH of the mixture was adjusted to 7 to afford a 6% hydrolyzed protein-based fire-extinguishing foam. According to the foaming tests by the Japanese Underwriter's Standards, this foam exhibited an expansion factor of 6.5, and a fire resistance of 5 minutes 10 seconds.

EXAMPLE 7

An 8% by weight aqueous solution of sodium chloride was added to dry cells of a methanol-assimilating bacterium (Pseudomonas japonica B-616; FERM P-2184) to form a 10% by weight suspension. The suspension was heated at 85 to 90° C. for 6 hours. The product was cooled, and centrifuged to separate the cells. The cells were washed once with water. Water was added to the cells to form a 20% by weight suspension. Then, 7% by weight, based on the weight of the dry cells, of potassium hydroxide was added, and the mixture was heated at about 100° C. for 6 hours. Further, 35% by weight, based on the weight of the dry cells, of calcium hydroxide was added, and the mixture was heated at about 100° C. for 4 hours. After cooling, water-insoluble substances were removed by centrifugal separation. Oxalic acid was added to the supernatant liquid of the centrifugal separation to adjust its pH to 6, and then it was concentrated. A small amount of a precipitate which formed during the concentration was separated by filtration, and the concentration was continued. The concentration was stopped when the specific gravity of the concentrate reached 1.2 (20° C.). The concentrate was cooled, and pentachlorophenol sodium salt, ferrous sulfate and ethylene glycol were added. The pH of the mixture was adjusted to 7 to prepare a 3% hydrolyzed protein-based fire-extinguishing foam. According to the foaming test by the Japanese Underwriter's Standards, this foam exhibited an expansion factor of 6.7 and a fire resistance of 5 minutes 20 seconds, and fully met the above Standards.

EXAMPLE 8

Water was added to the same bacterial cells as used in Example 1 to form a 10% by weight suspension, and an aqueous solution of sodium hydroxide was added to adjust its pH to 13. The mixture was heated at 60° to 70° C. for 2 hours to extract proteins. The insoluble residue was separated by centrifugal separation, and sulfuric acid was added to the liquid left after separation to adjust its pH to 4.2. The resulting precipitate (separated proteins) was centrifugally separated, and water was added to the separated proteins to form a 20% by weight suspension. To the suspension were added 50% by weight of calcium hydroxide and 2% by weight of sodium hydroxide, both based on the weight of the dry separated proteins, and the mixture was heated at about 100° C. for 7 hours. After cooling, insoluble substances were centrifugally separated, and hydrochloric acid was added to the supernatant liquid of the centrifugal separation to neutralize it to a pH of 6. It was then concentrated. The precipitate which formed during the concentration was removed by filtration. The filtrate was concentrated until its specific gravity reached 1.2 (20° C.). The concentrate was cooled, and sodium benzoate, ferrous chloride and ethylene glycol were added. The pH of the mixture was adjusted to 7 to afford a 3% hydrolyzed protein-based fire-extinguishing foam. According to the foaming test by the Japanese Underwriter's Standards, the foam exhibited an expansion factor of 7.2 and a fire-resistance of 6 minutes.

EXAMPLE 9

Sulfuric acid was added to a 10% by weight suspension of living cells separated from a culture broth of a methanol-assimilating bacterium (Pseudomonas methanolis BNK-84, FERM P-2247) to adjust its pH to 1.5. The suspension was then heated at 85° to 90° C. for 90 minutes. The product was cooled, and ammonia solution was added to adjust its pH to 3.8. The product was centrifuged, and washed once with water. Water was added to the bacterial cells to form a 20% by weight suspension. To the suspension were added 35% by weight of calcium hydroxide and 5% by weight of sodium hydroxide, both based on the cells, and the mixture was heated at 93° C. for 10 hours to decompose the cells. The product was hot-filtered through diatomaceous earth to separate insoluble substances. Hydrochloric acid was added to the filtrate to adjust its pH to 5.5. The resulting precipitate was separated by filtration, and the pH of the filtrate was adjusted to 7 with ammonia solution, and concentrated until its specific gravity reached 1.2 (20° C.). The precipitate which formed during the concentration was separated by filtration, and pentachlorophenol sodium salt, ferrous chloride, and ethylene glycol were added to the concentrated hydrolyzate. The pH of the mixture was adjusted to 7 to afford a 3% hydrolyzed protein-based fire-extinguishing foam.

A firefighting test was performed using the resulting foam in accordance with the National Test Standards (the Technical Standards of Fire-Extinguishing Foams, promulgated Dec. 9, 1975, Order No. 26, of the Ministry of Home Affairs, Japan). Good results were obtained.

Specifically, 320 liters of water and 200 liters of gasoline were placed in a square-shaped water tank made of iron and having a size of 2 m × 2 m × 0.3 m, and ignited. After a lapse of 1 minute from the ignition, a foam aqueous solution (3% premix type at 20° C.) was continuously issued from a blowing nozzle at a rate of 10 liters/min. under a pressure of 7.5 kg/cm$^2$.G. The fire was completely put out in 3.5 minutes. It also showed good results in a re-burning test. At this time, the foam showed an expansion factor of 7.9 which was comparable to that of the currently used products produced from keratin.

EXAMPLE 10

Water was added to the same dry bacterial cells as used in Example 1 to form a 10% by weight suspension Sulfuric acid was added to the suspension to adjust its pH to 1.2, and the mixture was heated at 85° to 90° C. for 20 minutes. After cooling, a 10% by weight aqueous solution of sodium hydroxide was added to adjust the pH to 4.2. The mixture was centrifuged. The separated liquid was discarded, and the cells were washed once with water. Water was added to the cells to form a 20% by weight suspension. To the suspension were added 30% by weight of calcium hydroxide and 5% by weight of sodium hydroxide, both based on the weight of the cells. The mixture was heated at about 100° C. for 7 hours to decompose the cells. The hydrolyzate was cooled, and centrifugally separated to remove insoluble substances. Hydrochloric acid was added to adjust the pH of the supernatant liquid. A small amount of a precipitate which formed at this time was separated by filtration. It was ascertained that this precipitate contained a major proportion of undecomposed protein, and a minor proportion of nucleic acid-related substances such as nucleosides, purine bases and pyrimidine bases. Ammonia solution was added to the filtrate to adjust its pH to 8. It was warmed to 50° C., and ammonium bicarbonate crystals were added to convert the dissolved calcium salt to calcium carbonate and precipitate it. The mixture was heated at 60° to 70° C. for 1 hour to complete the deposition of a precipitate and simultaneously, decompose the excess of the ammonium bicarbonate. After separating the precipitate of calcium carbonate, etc., the supernatant liquid was concentrated until its specific gravity reached 1.20 (20° C.). No deposition of a precipitate was observed during the concentrating operation. The total phosphorus content of the concentrate was 0.08% by weight, and the total phosphorus content of the starting bacterial cells was 1.2% by weight. Thus, most of phosphorus moved to the decomposition residue, the isoelectric point precipitate and the calcium carbonate precipitate. Further, the lipid content of the concentrated hydrolyzate was 0.3% by weight, and the starting cells had a liquid content of 10.5% by weight. Accordingly, most of the lipid moved to the decomposition residue. The amounts of nucleic acids and their related substances in the concentrate were only trace. When 0.2% by weight of pentachlorophenol sodium salt and 0.5% by weight, as Fe$^{2+}$, of ferrous chloride were added to the concentrate, they dissolved to form a clear solution. When this solution was stored for a half year at room temperature, no precipitate was formed, and it was very stable.

A concentrated hydrolyzate was obtained in the same way as above except that ammonium bicarbonate was not added. At this time, a small amount of precipitate formed during the concentrating operation. The precipitate was removed, and pentachlorophenol sodium salt and ferrous chloride were dissolved. The solution obtained was stored at room temperature, and when two months passed, a slight precipitate formed.

EXAMPLE 11

Water was added to the same dry cells as used in Example 5 to form a 17% by weight suspension, and to the suspension were added 20% by weight of calcium hydroxide, 5% by weight of magnesium oxide, 5% by weight of barium hydroxide, and 18% by weight of potassium hydroxide. The mixture was heated at about 100° C. for 8 hours to decompose the cells. The hydrolyzate was hot-filtered through ditomaceous earth to remove the insoluble substances. Sulfuric acid was added to the filtrate to adjust its pH to 5, and the precipitated unreacted proteins, barium sulfate, etc. were removed by filtration. To the filtrate was added an aqueous solution of sodium hydroxide to adjust its pH to 7.5. It was warmed to 50° C. and ammonium bicarbonate crystals were added to convert the dissolved calcium, magnesium and barium salts to calcium, magnesium and barium carbonate and precipitate them. After heating at 60° to 70° C. for 1.5 hours, these precipitates were separated by filtration. The filtrate was concentrated until its specific gravity reached 1.2 (20° C.). There was no deposition of a precipitate during the concentration. The total phosphorus content of the concentrated hydrolyzate was 0.18% by weight, and starting cells had a total phosphorus content of 2.6% by weight. Accordingly, most of phosphorus moved to the decomposition residue, the isoelectric precipitate and carbonate precipitate. The concentrated hydrolyzate had a lipid content of 7.5% by weight, and the starting cells had a lipid content of 7.5% by weight. Accordingly, most of a lipid moved to the decomposition residue. When 0.3% by weight of sodium benzoate and 0.4% by weight, as Fe$^{2+}$, of ferrous sulfate were added to the concentrated hydrolyzate, they dissolved to form a clear solution. When this solution was stored at room temperature for half a year, no decomposition of a precipitate was observed.

EXAMPLE 12

Water was added to dry cells of a glucose-assimilating bacterium (Protaminobacter rubber, ATCC-8457) to form a 17% by weight suspension. To the suspension were added 30% by weight of calcium hydroxide and 10% by weight of sodium hydroxide, based on the weight of the dry cells. The mixture was heated at about 100° C. for 10 hours to decompose the cells. The hydrolyzate was cooled, and centrifuged to remove insoluble substances. Sulfuric acid was added to the supernatant liquid of the centrifugal separation to adjust its pH to 4.3. The precipitated undecomposed proteins, etc. were separated by filtration, and an aqueous solution of sodium hydroxide was added to the filtrate to adjust its pH to 7.5. It was warmed to 50° C. and ammonium bicarbonate crystals were added to convert the dissolved calcium salt to calcium carbonate and precipitate it. The mixture was heated at 60° to 70° C. for 1.5 hours, and the precipitate of calcium carbonate, etc. was separated by filtration, and the filtrate was concentrated until its specific gravity became 1.19. No deposition of a precipitate was observed during the concentrating operation. The concentrated hydrolyzate was cooled, and pentachlorophenol sodium salt, ferrous chloride and ethylene glycol were added. The pH was adjusted to 7 to afford a 3% hydrolyzed protein-based fire-extinguishing foam. According to the test of the Japanese Underwriter's Standards, the foam exhibited an expansion factor of 6.5, and a fire resistance of 5 minutes 45 seconds, and fully met the above standards. When the foam was subjected to a degeneration test (heated at 65° C. for 24 hours), scarcely any change was observed in its specific gravity, pH and viscosity. In a precipitation test, the foam showed only a trace of precipitation both in fresh water and in artificial sea water.

EXAMPLE 13

Yeast cells were obtained by centrifugal separation from a culture broth of a glucose-assimilating yeast (Candida tropicalis, IFO-1401). Water was added to the cells to form an 8% by weight suspension. The cells were disrupted using a vibratory glass bead mill. To the disrupted cells were added 35% by weight of calcium hydroxide and 10% by weight of sodium hydroxide, both based on the weight of the dry cells. The mixture was heated at about 100° C. for 10 hours to decompose the cells, and hot-filtered through diatomaceous earth to remove water-insoluble substances. Hydrochloric acid was added to the filtrate to adjust its pH to 3.5. The precipitated undecomposed proteins, etc. were separated by filtration, and ammonia solution was added to adjust the pH of the filtrate to 9. Carbon dioxide was blown into the filtrate to convert the dissolved calcium salt to calcium carbonate and precipitate it. At this time, ammonia solution was freshly added, as desired, to maintain the pH always at 8 or more. The mixture was heated at 60° to 80° C. for 1 hour, and filtered to separate the precipitate containing calcium carbonate, etc. The filtrate was concentrated until its specific gravity became 1.15 (20° C.). During this time, no deposition of a precipitate was observed. After cooling, sodium benzoate, ferrous chloride and ethylene glycol were added, and the pH of the mixture was adjusted to 7 to afford a 6% hydrolyzed protein-based fire-extinguishing foam. According to the test specified in the Japanese Underwriter's Standards, the foam exhibited an expansion factor of 6.3, and a fire resistance of 5 minutes 30 seconds. In the same degeneration test as in Example 12, no change was observed in any of the items examined.

EXAMPLE 14

Water was added to the same bacterial cells as used in Example 12 to form a 10% by weight suspension, and while the suspension was neutral (pH 6.5), it was heat-treated at 90° C. for 2 hours. After cooling, sulfuric acid was added to adjust the pH to 4.5, and the mixture was centrifuged. The supernatant liquid resulting from the centrifugal separation was discarded, and the bacterial cells were washed once with water. Water was added to the treated cells to form a 20% by weight suspension. To the suspension was added 8% by weight of sodium hydroxide, and the mixture was heated at about 100° C. for 4 hours. Then, on the same basis, 30% by weight of calcium hydroxide was added, and the mixture was heated for 2 hours to decompose the cells. The hydrolyzate was hot-filtered through diatomaceous earth to separate insoluble substances. Hydrochloric acid was added to the filtrate to adjust its pH to 3.0. The resulting precipitates such as undecomposed proteins were separated by filtration. Ammonia solution was added to the filtrate to adjust its pH to 8. It was warmed to 50° C., and ammonium carbamate crystals were added. The mixture was further heated at 60° to 70° C. for 1 hour. The precipitate containing calcium carbonate, etc. was separated by filtration, and the filtrate was concentrated until its specific gravity reached 1.19 (20° C.). No deposition of a precipitate was observed during the concentrating operation. After cooling, pentachlorophenol sodium salt, ferrous sulfate and propylene glycol were added, and the pH of the mixture was adjusted to 7 to afford a 3% hydrolyzed protein-based fire-extinguishing foam. According to the foaming test by the Japanese Underwriter's Standards, the foam exhibited an expansion factor of 7.1. and a fire resistance of 5 minutes 30 seconds. In the same degeneration test as in Example 12, no change was observed in any of the items examined.

EXAMPLE 15

Bacterial cells separated by centrifugal separation from a culture broth of the same cells as used in Example 9 were made into a 15% by weight suspension. To the suspension were added 15% by weight of barium hydroxide and 20% by weight of sodium hydroxide, both based on the weight of the dry bacterial cells. The mixture was heated at about 115° C. under an elevated pressure for 6 hours to decompose the cells. The hydrolyzate was cooled, and centrifuged to remove insoluble substances. Sulfuric acid was added to the supernatant liquid resulting from the centrifugal separation to adjust its pH to 5.0. The precipitate containing undecomposed proteins, barium sulfate and nucleic acid related substances, etc. was separated by filtration. Ammonia solution was added to the filtrate to adjust its pH to 9. Ammonium bicarbonate was added to precipitate barium carbonate, etc. After heating at 60° to 70° C. for 1.5 hours, these precipitates were separated by filtration. The filtrate was concentrated until its specific gravity became 1.18 (20° C.). No deposition of a precipitate was observed during the concentrating operation. After cooling, sodium benzoate, ferrous sulfate and propylene glycol were added, and the pH of the mixture was adjusted to 7 to afford a 3% hydrolyzed protein-based fire-extinguishing foam. According to the foaming test by the Japanese Underwriter's Standards, the foam showed an expansion factor of 6.1, and a fire resistance of 5 minutes 50 seconds. In the same degeneration test as in Example 12, no change was observed in any of the items examined.

EXAMPLE 16

Water was added to dry cells of a glucoseassimilating bacterium (Pseudomonas extorquens, NCIB 9399) to form a 17% by weight suspension. To the suspension were added 35% by weight of calcium hydroxide and 5% by weight sodium hydroxide, both based on the weight of the dry cells. The mixture was heated at about 100° C. for 10 hours. After cooling, the hydrolyzate was centrifuged to separate insoluble substances. Hydrochloric acid was added to the supernatant liquid resulting from the centrifugal separation to adjust its pH to 4.5. The resulting precipitate was separated by filtration, and ammonia solution was added to the filtrate to adjust its pH to 8. Then, the filtrate was heated to 50° C., and ammonium bicarbonate crystals were added to convert the dissolved calcium salt to calcium carbonate and precipitate it. The mixture was heated at 60° to 70° C. for 0.5 hour, and the precipitates such as calcium carbonate were separated. The filtrate was concentrated until its specific gravity reached 1.19 (20° C.). After cooling, pentachlorophenol sodium salt, ferrous chloride and ethylene glycol were added. The pH of the mixture was adjusted to 7 to afford a 3% hydrolyzed protein-based fire-extinguishing foam.

The fire-extinguishing foam was subjected to a performance test by a method in accordance with the National Test Standards used in Example 9. In a fire extinguishing test (3% premix) using fresh water, the fire was completely put out in 3 minutes 40 seconds. At this time, the foam exhibited an expansion factor of 7.94. In a fire extinguishing test using artificial sea water, the fire was completely extinguished in 3 minutes 45 seconds with the 3% premix. The foam exhibited an expansion factor of 8.2 at this time. In a degeneration test of the fire-extinguishing foam (maintained at 65° C. for 216 hours, and then the temperature was returned to room temperature), no change was observed in its pH, specific gravity and viscosity, and no change was seen either in sedimentability and precipitating property (in fresh water and artificial sea water).

EXAMPLE 17

Sulfuric acid was added to a suspension (10% by weight) of the living cells obtained in the same way as in Example 8 to adjust its pH to 1.5. The mixture was heated at 85° to 90° C. for 30 minutes. After cooling, ammonia solution was added to adjust the pH of the mixture to 4.2. It was then centrifuged, and the cells were washed once with water. Water was added to the treated cells to afford a 20% by weight suspension. To the suspension were added 40% by weight of calcium hydroxide and 4% by weight of sodium hydroxide, based on the weight of the dry cells. The mixture was heated at about 100° C. for 10 hours, and hot-filtered through diatomaceous earth to remove insoluble substances. Hydrochloric acid was added to the resulting filtrate to adjust its pH to 4.2. The resulting precipitate was separated by filtration, and ammonia solution was added to the filtrate to adjust its pH to 8. Then, ammonium carbonate was added to precipitate calcium carbonate. The excess of the ammonium carbonate was decomposed by heating at 60° to 70° C. for 1 hour, and the mixture was filtered. The filtrate was concentrated until its specific gravity became 1.2 (20° C). No formation of a precipitate was observed during this time. After cooling, pentachlorophenol sodium salt, ferrous chloride and ethylene glycol were added to the concentrated hydrolyzate. The pH of the mixture was adjusted to 7 to afford a 3% hydrolyzed protein-based fire-extinguishing foam.

The product was subjected to a performance test in the same way as in Example 9. In a fire-extinguishing test (3% premix type) using fresh water, the fire was completely put out in 3 minutes 4 seconds. At this time, the foam showed an expansion factor of 8.3. In a fire-extinguishing test using artificial sea water, the fire was completely put out in 3 minutes 8 seconds using the same 3% premix type. The expansion factor of the foam at this time was 8.2. In a re-burning test, the foam obtained in this Example met all the standards. In a degeneration test for fire-extinguishing foams, no change was seen in any of the items examined.

EXAMPLE 18

The same bacterial cells as used in Example 12 were decomposed by the same method as in Example 12. Insoluble substances were removed, and the pH of the remaining liquid was adjusted to 6 with hydrochloric acid. A small amount of a precipitate which formed was separated by filtration. The filtrate was heated to 50° C., and ammonium bicarbonate crystals were added. Subsequently, the mixture was heated at 60° to 70° C. for 1.5 hours. The precipitates such as calcium carbonate were separated by filtration. Upon cooling the filtrate, a precipitate was formed again. When the precipitate was separated by filtration and the filtrate was concentrated, a precipitate also formed during the concentration. Thus, filtration was performed every time a precipitate was formed. The concentrating operation was stopped when the specific gravity of the filtrate became 1.19 (20° C.). When the concentrated hydrolyzate was stored at room temperature, a precipitate formed again. These precipitates were analyzed and found to be not inorganic salts such as calcium carbonate but composed mainly of ingredients constituting nucleic acids, such as nucleosides, purine bases and pyrimidine bases. Pentachlorophenol sodium salt, ferrous chloride, and ethylene glycol were added to the concentrated hydrolyzate, and the ph of the mixture was adjusted to 7 to form a 3% hydrolyzed protein-based fire-extinguishing foam. According to the Japanese Underwriter's Standards, the foam exhibited an expansion factor of 6.3 and a fire resistance of 5 minutes 30 seconds, and met the above Standards. In the same degeneration test as in Example 12, the viscosity of the foam increases, and a precipitate formed.

EXAMPLE 19

Water was added to the dried excess sludge resulting from the activated sludge process (containing 95% by weight of microbial cells) formed in an organic synthetic chemical plant to a concentration of 10% by weight. The suspension was heated at 90° C. for 2 hours. After cooling, the treated sludge was separated by centrifugal separation. Water was added to the treated sludge to form a 15% by weight suspension, and 5% by weight of sodium hydroxide and 35% by weight of calcium hydroxide, both based on the weight of the cells, were added. The mixture was heated at 96° to 98° C. for 7.5 hours. The hydrolyzate was cooled, and centrifuged to separate insoluble substances. Hydrochloric acid was added to the supernatant liquid resulting from the centrifugal separation to adjust its pH to 4.2, and the precipitate containing undecomposed proteins, etc. was separated by filtration. An aqueous solution of sodium hydroxide was added to the filtrate to adjust its pH to 7.6. After heating it to 40° C., ammonium bicarbonate crystals were added. The mixture was maintained at 60° to 80° C. for about 1 hour, and then the precipitate including calcium carbonate, etc. was separated by filtration. The filtrate was concentrated until its specific gravity became 1.19 (20° C.). No formation of a precipitate during the concentrating operation was observed. After cooling, pentachlorophenol sodium salt and a ferrous salt were added. The pH of the mixture was adjusted to 7 to afford a 3% hydrolyzed protein-based fire-extinguishing foam. In the foaming test by the Japanese Underwriter's Standards, the foam exhibited an expansion factor of 6.5 and a fire resistance of 5 minutes.

EXAMPLE 20

Sulfuric acid was added to a fermentation residue (a microbial cell content of 90% by weight) from the fermentation of amino acids using an amino acid-producing bacterium (Brevibacterium ammoniagenes, IFO 12612) to form a 9% by weight suspension having a pH of 0.5. The suspension was heated at 90° C. for 30 minutes. After cooling, an aqueous solution of sodium hydroxide was added to adjust the pH to 4.1. The suspension was then centrifuged to separate the pre-treated cells. The cells were washed once with water, and water was added to form a 15% by weight suspension. Sodium hydroxide and calcium hydroxide were added to the suspension in an amount of 6% weight and 37% by weight respectively based on the weight of the dry microbial cells. The mixture was then heated at about 100° C. for 7 hours.

After cooling, the product was centrifuged to separate insoluble substances. Hydrochloric acid was added to the supernatant liquid resulting from the centrifugal separation to adjust its pH to 3.8. The precipitate which formed was separated by filtration. An aqueous solution of sodium hydroxide was added to the filtrate to adjust its pH to 7.8, and it was heated on a hot water bath. When its temperature reached 40° to 50° C., ammonium bicarbonate crystals were added, and the mixture was maintained at 60° to 80° C. for 1 hour. The precipitate containing calcium carbonate, etc. was separated by filtration. The filtrate was concentrated until its specific gravity reached 1.19 (20° C.). After cooling, ferrous sulfate and pentachlorophenol sodium salt were added to the concentrated hydrolyzate, and the pH of the mixture was adjusted to 7 to afford a 3% hydrolyzed protein-based fire-extinguishing foam. According to the performance test by the Japanese Underwriter's Standards, the foam exhibited an expansion factor of 6.8 and a fire resistance of 5 minutes 20 seconds.

What we claim is:

1. A process for decomposing microbial cells to obtain foamable hydrolyzed proteins, which comprises treating the microbial cells with an alkaline aqueous solution containing an alkaline earth metal hydroxide and an alkali metal hydroxide, said alkaline earth metal hydroxide being at least one compound selected from the group consisting of calcium hydroxide, barium hydroxide and magnesium hydroxide, and said alkali metal hydroxide being at least one compound selected from the group consisting of sodium hydroxide and potassium hydroxide, the alkaline earth metal hydroxide being 15 to 50% by weight and the amount of the alkali metal hydroxide being 2 to 20% by weight, both based on the weight of the microbial cells.

2. The process of claim 1 wherein the microbial cells are untreated microbial cells.

3. The process of claim 1 which further includes removing the hydrolysis residue from the alkaline aqueous solution, adjusting the pH of the filtrate to 3–7.5, coagulating and separating the unreacted proteins, adding a carbonic acid compound to the supernatant liquid under alkalinity, and separating and removing the dissolved alkaline earth metal compound as an alkaline earth metal carbonate.

4. The process of claim 3 wherein the carbonic acid compound is a carbonate of ammonium.

* * * * *